United States Patent
Fuger et al.

[11] 3,946,014
[45] Mar. 23, 1976

[54] PROCESS FOR PREPARING CERTAIN 1,3,4-DIOXAZOL-2-ONES AND PRODUCTS

[75] Inventors: Karl E. Fuger, Allschwil, Switzerland; Emmett H. Burk, Jr., Glenwood, Ill.

[73] Assignee: Atlantic Richfield Company, Los Angeles, Calif.

[22] Filed: Mar. 26, 1973

[21] Appl. No.: 344,678

Related U.S. Application Data

[63] Continuation-in-part of Ser. No. 85,821, Oct. 30, 1970, abandoned.

[52] U.S. Cl.... 260/268 C; 260/77.5 R; 260/293.67; 260/307 A
[51] Int. Cl.² .................................. C07D 295/14
[58] Field of Search........ 260/307 A, 268 C, 293.67

[56] References Cited
UNITED STATES PATENTS

| | | | |
|---|---|---|---|
| 3,609,163 | 9/1971 | Burk et al. | 260/307 A |
| 3,737,435 | 6/1973 | Burk et al. | 260/307 A |

OTHER PUBLICATIONS
Wagner et al., – "Synthetic Organic Chemistry" John Wiley & Sons, New York (1953) – pp. 483–484, 646.

*Primary Examiner*—Raymond V. Rush
*Attorney, Agent, or Firm*—Coleman R. Reap

[57] ABSTRACT

Cyclic nitrile carbonate group-containing chloroformate of the general formula:

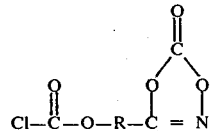

is condensed with polyfunctional nucleophilic compound of the general formula:

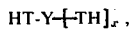

wherein R is an aliphatic hydrocarbon, T is O, S or NR', wherein R' is hydrogen or an essentially hydrocarbonaceous group, Y consists essentially of carbon and hydrogen, and $x$ is 1 to 3, to yield hydrogen chloride as the elimination product and cyclic nitrile carbonate group-containing condensate of the general formula:

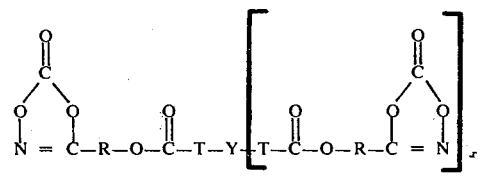

as the addition product. The addition product is useful as, inter alia, a precursor for a carbonate, urethane or thiocarbonate group-containing polyurethane, polyurea, or polythiourethane, these polymers being in turn useful in coating, molding, adhesive, and the like compositions.

11 Claims, No Drawings

PROCESS FOR PREPARING CERTAIN 1,3,4-DIOXAZOL-2-ONES AND PRODUCTS

This application is a continuation-in-part application of U.S. patent application Ser. No. 85,821, filed Oct. 30, 1970 now abandoned.

The present invention relates to novel chemical compounds and their synthesis. More particularly, it is concerned with the discovery that certain cyclic nitrile carbonate group-containing chloroformates will undergo a chain-extending, condensation reaction with certain polyfunctional nucleophilic compounds to yield hydrogen chloride as the elimination product and a cyclic nitrile carbonate group-containing condensate as the addition product.

In U.S. Pat. No. 3,609,163, herein incorporated by reference, are disclosed, inter alia, cyclic nitrile carbonate group-containing chloroformates of the general formula:

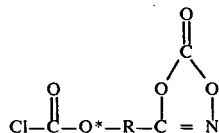

wherein R is aliphatic hydrocarbon of 2 to 11 carbon atoms, at least 2 carbon atoms of which separate the non-ring oxygen atom (the one identified by an asterisk in the above formula) from the nitrile carbon atom. These chloroformates are disclosed in the above-mentioned U.S. Patent as being useful as blowing agents for vinyl resins and the like and, as regards certain ones of the chloroformates, as being useful as precursors for ethylenically-unsaturated cyclic nitrile carbonate compounds. It has now been found that useful cyclic nitrile carbonate group-containing condensates can be prepared from the above-described chloroformates wherein R is a linear or branched chain saturated, ethylenically unsaturated or acetylenically unsaturated hydrocarbon radical by condensing the latter with polyfunctional nucleophilic compounds of the general formula:

wherein each T is O, S, or NR'; Y is an organic radical which is essentially hydrocarbonaceous; and x is 1 to 3, preferably 1 or 2. R' is hydrogen or an essentially hydrocarbonaceous organic radical which is either monovalent and bonded only to the nitrogen atom or is divalent and is additionally bonded either to Y (as, for example, in 3-aminopiperidine) or to another nitrogen atom of another T (as, for example, in piperazine). R' generally has up to 40 carbon atoms and often has 10 carbon atoms or less. By the reference to Y and R' being "essentially hydrocarbonaceous" is meant that those groups consist of carbon and hydrogen as essential components, thus recognizing that while elements other than carbon and hydrogen can be present, either in pendant moieties or in a main chain, they must not change the characteristic intended for Y and R', that is, that they be free of groups that would be reactive with the cyclic nitrile carbonate group-containing chloroformate, such as reactive hydrogen-containing groups as determined by the Zerewitinoff test. The products of the condensation reaction are hydrogen chloride and an addition product which contains carbonate, urethane or thiocarbonate linking groups. The reaction can be represented by the following equation, R, Y, T, and x being as defined above:

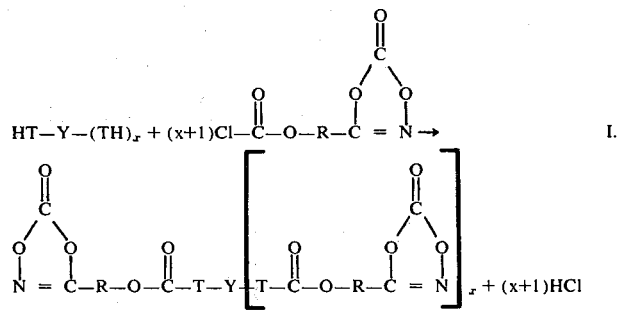

where, however, the T of a -TH group of the nucleophilic reactant is NR' and R' is hydrogen (i.e., the —TH group is an NH₂ group), then T in the addition product of the condensation reaction can be either >NH or

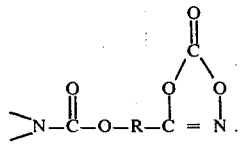

The latter moiety is provided where a molar equivalent of —NH₂ groups in the nucleophilic reactant is condensed with two moles of the chloroformate.

The novel addition products produced by the condensation reaction of the present invention are useful as, inter alia, precursors for carbonate, urethane or thiocarbonate group-containing polyurethanes, polyureas, polythiourethanes, and polymers of mixed urethane, urea, and/or thiourethane linkages. These polymers are, in turn, useful in coating, adhesive, fibre-forming, sealing, and molding compositions. Preparation of the polymers is disclosed, for example, in Belgian Pat. No. 706,181, as well as in U.S. Pat. Nos. 3,531,425 and 3,652,507, herein incorporated by reference. Briefly, the polymers can be prepared by condensing the cyclic nitrile carbonate groups of the addition products of this invention with a polyfunctional amine, alcohol, or mercaptan, such as the polyfunctional nucleophilic compound employed in the present invention. The condensation occurs at elevated temperatures and can be catalyzed by, for example, a catalytic combination of a first metal from Groups III–V of the Periodic Chart, e.g., tin, and a second metal from Groups I or II of the iron series of Group VIII, e.g., sodium. The condensation reaction which takes place between the groups can be understood from the following partial reaction equation which depicts ethylene glycol being condensed with two cyclic nitrile carbonate groups:

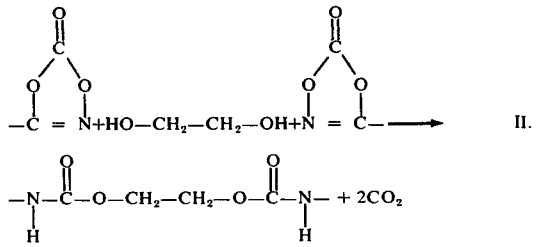

A method for preparing the chloroformate starting material used in the reaction of the present invention is disclosed in the aforementioned U.S. Pat. No. 3,609,163. Briefly, the chloroformates can be prepared by phosgenating a hydroxyl group-containing monohydroxamic acid, for example as represented in the following equation:

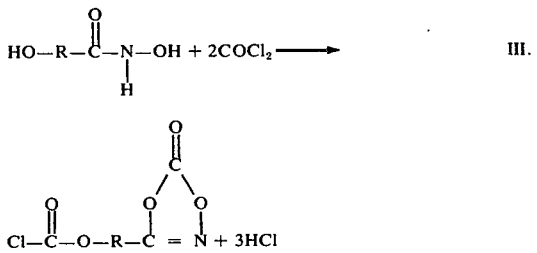

The hydroxyl group-containing hydroxamic acid can, in turn, be prepared by reacting a lactone with hydroxylamine, as represented in the following equation:

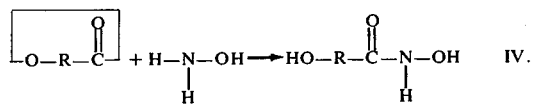

Branched chain as well as unbranched, and saturated as well as unsaturated, chloroformates can be employed in the present invention. In the above-discussed method of preparing the chloroformates, however, it is generally preferred that the R group be unbranched rather than branched, and saturated rather than unsaturated. Accordingly, the chloroformate used in the present invention will most often be so composed; also, its R group will frequently contain from 2 to 5 carbon atoms.

Where the chlorocarbonyloxy group of the chloroformate is separated from the cyclic nitrile carbonate group by a paraffinic carbon-to-carbon chain of 2 carbon atoms, then the chloroformate is capable of partially decomposing to yield ethylenically-unsaturated cyclic nitrile carbonate compounds. As discussed in the aforementioned U.S. Pat. No. 3,609,163, the decomposition is catalyzed by organic tertiary amines which have pK values below about 5. As will be hereinafter discussed in greater detail, it can be advantageous to include a basic compound such as a tertiary amine in the condensation reaction mixture of the present invention. Where such is used, then it will be preferred that the chloroformate starting material have at least 3 carbon atoms of R separating the non-ring oxygen atom from the nitrile carbon atom, the purpose being to avoid the situation wherein an unsaturation-yielding partial decomposition reaction would compete with the desired condensation reaction of the present invention. Most preferably, in fact, the minimum 3 carbon atom separation is employed regardless of whether a basic compound is present in the condensation reaction mixture.

Most preferably, the chloroformate is soluble in one or more of the following solvents: water, chloroform, diethyl ether, benzene, and p-dioxane. This solubility permits the use of one or more of those solvents in the condensation reaction, which, as hereinafter discussed, is the preferred manner of conducting the reaction. As examples of preferred chloroformates can be mentioned, then 5-(chlorocarbonyloxy)-pentane-1-nitrile carbonate, 4-(chlorocarbonyloxy)butane-1-nitrile carbonate, and 3-(chlorocarbonyloxy)propane-1-nitrile carbonate.

The polyfunctional nucleophilic compound generally has a molecular weight of up to about 10,000, most often of up to about 1,000 or about 5,000, of which Y generally amounts to up to about 9,900, most often up to about 900 or about 4,900. The nucleophilic compound can be aromatic or non-aromatic (i.e., aliphatic or cycloaliphatic) and the nucleophilic groups (i.e., those designated as —TH in the above formula) can be held either by non-aromatic carbon atoms or by aromatic carbon atoms (i.e., attached directly to an aromatic ring). Where the nucleophilic compound is non-aromatic, it can be saturated or ethylenically or acetylenically unsaturated. Where the nucleophilic groups are held by non-aromatic carbon atoms, they (the nucleophilic groups) can be primary, secondary, or tertiary. (To clarify, by a primary nucleophilic group is meant one which is held by a carbon atom which also holds 2 hydrogen atoms.) Where the nucleophilic compound is aromatic, it is often preferred that it contain either 1 or 2 benzene rings; and, if the latter, preferably non-fused rings. As examples of suitable nucleophilic compounds wherein Y is hydrocarbyl can be mentioned, then alkanediols, dithiols, and diamines such as ethylene glycol, 1,4-butanediol, 1,6-hexanediol, dihydroxylated polybutadiene, 1,2-ethanedithiol, 1,4-butanedithiol, hexamethylene diamine, and ethylene diamine; di(hydroxyalkyl)benzenes, di(mercaptoalkyl)benzenes, and di(aminoalkyl)benzenes such as 1,4-di(hydroxymethyl)benzene, 1,3-di(mercaptopropyl)-benzene, and 1,4-bis(N-methylaminomethyl)-benzene; di(hydroxyphenyl)alkanes, di(mercaptophenyl)alkanes, and di(aminophenyl)alkanes such as 2,2-bis-(4-hydroxyphenyl)-propane, bis(3-mercaptophenyl)methane, and 1,2-bis(4-aminophenyl)ethane; alkane triols, trithiols, and triamines, such as glycerine, 1,3,6-trimercaptohexane and 1-(N-ethylamino)-3,5-diaminopentane; and alkane tetraols, tetrathiols, and tetraamines such as pentaerythritol, 1,3,5,7-tetramercaptoheptane, and 1,1,4,4-tetraaminobutane.

Also suitable as nucleophilic reactants in the process of the present invention are compounds containing any of the several possible combinations of the different suitable nucleophilic groups, such as, for example, aminoalcohols, mercaptoamines, hydroxymercaptans, etc.

As with the chloroformate, it is preferred that the nucleophilic reactant be soluble in one or more of the following solvents: water, chloroform, diethyl ether, benzene, and p-dioxane.

As stated above, Y in the formula for the nucleophilic compound can contain non-interfering atoms of elements other than carbon and hydrogen, e.g., can contain carbonyl oxygen, thiocarbonyl sulfur, amido nitrogen, ether oxygen, thioether sulfur, etc. As examples of such compounds can be mentioned, for instance, nucleophilic group-containing amides, esters, thioesters, ethers, thioethers, and di-substituted amines.

A prime example of suitable nucleophilic group-containing esters is polyhydroxyl group-containing polyesters. Suitable such hydroxyl group-containing polyesters are the well known condensation products of polycarboxylic acids, for instance, of 5 to 15 carbon atoms, or their anhydrides, and polyhydric alcohols, such as those of about 2 to 15 carbon atoms. As suitable polycarboxylic acids may be mentioned, for example, aromatic acids such as benzene-1,3-dicarboxylic acid and benzene-1,2-dicarboxylic acid, and aliphatic acids, either saturated or unsaturated, such as adipic acid, azelaic acid, sebacic acid, adducts of maleic acid with fatty oils or fatty oil acids such as, for example, tall oil, linoleic acid, etc. Suitable polyhydric alcohols include those mentioned above as being suitable for use as the polyhydroxyl compound in this invention, for example, ethylene glycol, glycerine, pentaerythritol, etc. Preferably at least two of the polyester's hydroxyl groups are primary hydroxyl groups.

Prime examples of suitable nucleophilic group-containing ethers are polyhydric alkylene ethers, including poly-(alkylene ethers), having a molecular weight of up to about 3000, preferably up to about 1000. Suitable such polyhydric alkylene ethers may be derived, for example, by the polymerization of alkylene oxides such as ethylene oxide, propylene oxide, butylene oxide, and the like. They may also be prepared by the polymerization of the cyclic ethers such as, for example, dioxane, tetrahydrofuran, and the like, and by the condensation of an alkylene oxide with a polyol, e.g., a glycol such as ethylene glycol, propylene glycol, butylene glycol, and the like, or a triol such as trimethylolethane, trimethylolpropane, and the like. Often preferred are those poly-(alkylene ether) glycols wherein the repeating alkylene group has from 2 to 4 carbon atoms.

As examples of suitable nucleophilic group-containing thioethers can be mentioned, for instance, the polymercapto alkylene thioether equivalents of the polyhydric alkylene ethers mentioned above. Thus, for example, the compound 1-hydroxy-2-(hydroxyethoxy)ethane exemplifies a suitable nucleophilic group-containing ether for use as the nucleophilic compound in the present invention; its polymercapto alkylene thioether equivalent is 1-mercapto-2-(mercaptoethylthio)ethane, which exemplifies a suitable nucleophilic group-containing thioether for use as the nucleophilic compound in the present invention.

The condensation reaction of the present invention can generally be conducted at a temperature above about $-10°C$. but below that at which the cyclic nitrile carbonate ring reacts with the nucleophilic compound and below the point of decomposition (e.g., to an isocyanate) or the desired addition product, for example, in the range of $-10°$ to $60°C$., preferably about $20°$ to $40°$ or $50°C$. Control of the temperature of the reaction, which is exothermic, can be achieved, for example, by effecting gradual addition of the nucleophilic reactant to the chloroformate, or by contacting the reaction mixture with a cooling medium, or by employing both means.

To insure a fast rate of reaction, it is preferred that the condensation be conducted while the reactants are in contact with a hydrogen chloride acceptor. Generally suitable hydrogen chloride acceptors are basic materials which are non-reactive with the reactants or the addition product but which are effective to neutralize the hydrogen chloride produced. Most preferably the amount of HCl acceptor employed will be at least that which is stoichiometrically required. Inorganic bases, such as the alkali metal hydroxides, carbonates, and bicarbonates, e.g., sodium hydroxide, carbonate, and bicarbonate, as well as organic bases, such as the nitrogenous bases, e.g., pyridine, tertiary amines such as N,N-dimethylaniline, etc., can be used as the HCl acceptor.

Bases, most especially organic bases, often tend to catalyze a reaction between reactive hydrogen-containing groups and cyclic nitrile carbonate groups. Therefore, when a basic HCl acceptor is employed in the present process, it is preferred that essentially no excess of the polyfunctional nucleophilic compound be employed. Thus, at least a stoichiometric amount of the chloroformate is preferably used in that circumstance.

The reaction is carried out with the reactants being homogeneously mixed together, either in the presence or absence of an inert solvent. The presence of a solvent for both reactants is preferred, however. Suitable solvents include, for example, p-dioxane, chloroform, diethyl ether, and benzene. Mixtures of solvents, even mutually immiscible solvents such as chloroform and water, or diethyl ether and water, can also be used if desired. It is preferred that the reaction mixture be agitated during the condensation reaction, especially when a mixture of immiscible solvents is employed, since in this case the condensation often takes place at the solvent interface.

Recovery of the addition product from the reaction mixture can be by any suitable means, such as, for example, by solvent extraction methods. Where a hydrogen chloride acceptor has been used, it is generally preferred to neutralize any unreacted amounts thereof which might be present in the crude mixture. This can conveniently be accomplished by washing the mixture with a dilute aqueous solution of an acid such as HCl.

The invention will be better understood by reference to the following examples.

EXAMPLE I

There are dissolved in 50 ml. of para-dioxane, at room temperature, 11.78 g. (0.05 mole) of 5-(chlorocarbonyloxy)pentane-1-nitrile carbonate and 2.25 g. (0.025 mole) of 1,4-butanediol. To that well-stirred solution is then added, over a period of 13 minutes, a solution of 3.95 g. (0.05 mole) of pyridine in 10 ml. of para-dioxane. The temperature of the reaction solution rises during the addition of about 29°C., and the solution acquires a faint purple color which disappears by the end of the addition. After a total reaction time of 35 minutes, the solution is cooled to about 20°C. and 150 ml. of chloroform is added thereto. The resultant mixture is washed with slightly acidic water (e.g., an aqueous solution of HCl) and then with plain water to effect removal of the para-dioxane, the pyridine hydrochloride, and any unreacted pyridine. The chloroform layer is then dried over magnesium sulfate and then stripped under vacuum to give about 11 g. (representing a yield of about 90% of theoretical) of a thick oil which is identified by elemental, infrared, and nuclear magnetic resonance analyses as crude 1,4-bis(5-(nitrilecarbonato)pentoxycarbonyloxy)butane, which can be represented by the structural formula:

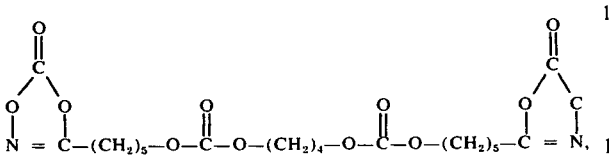

containing some 5-chloropentane-1-nitrile carbonate as impurity.

EXAMPLE II

There are dissolved in 75 ml. of para-dioxane, at room temperature, 23.56 g. (0.10 mole) of 5(chlorocarbonyloxy)-pentane-1-nitrile carbonate and 5.91 g. (0.05 mole) of 1,6-hexanediol. To that well-stirred solution is then added, over a period of 33 minutes, a solution of 7.91 g. (0.10 mole) of pyridine in 25 ml. of para-dioxane. The temperature of the reaction solution is held to about 30°C. and the solution is stirred for an additional hour after completion of the addition. The solution is then cooled to below 10°C. and 300 ml. of chloroform is added thereto. The resultant mixture is washed with slightly acidic water (e.g., an aqueous solution of HCl) and then with plain water to remove the para-dioxane, the pyridine hydrochloride, and any unreacted pyridine. The chloroform layer is then dried over magnesium sulfate and then stripped under vacuum to give about 23.7 g. (representing a yield of about 92% of theoretical) of an oil which is identified by elemental, infrared, and nuclear magnetic resonance analyses as crude 1,6-bis(5-nitrilecarbonato)pentoxycarbonyloxyl) hexane, which can be represented by the structural formula:

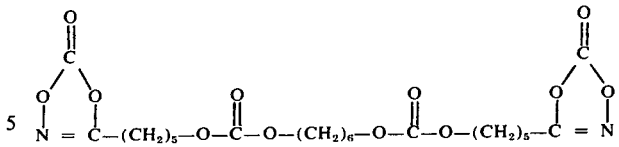

EXAMPLE III

The procedure of Example II is repeated, but instead using a solution of 25.39 g. (0.108 mole) of the chloroformate and 7.45 g. (0.054 mole) of 1,4-di(hydroxymethyl)benzene in 110 ml. of para-dioxane and a solution of 8.53 g. (0.108 mole) of pyridine in 25 ml. of para-dioxane. There is obtained 26.4 g. (representing a yield of 91% of theoretical) of an oil which is identified by elemental, infrared, nuclear magnetic resonance, and mass spectroscopy analyses as 1,4-bis(5-(nitrilecarbonato)pentoxycarbonyloxymethyl)benzene, which can be represented by the structural formula:

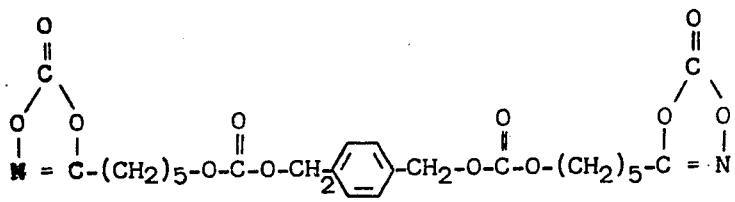

EXAMPLE IV

The procedure of Example II is repeated, but instead using a solution of 47.12 g. (0.20 mole) of the chloroformate and 22.83 g. (0.10 mole) of 2,2-bis(4-hydroxyphenyl)propane in 160 ml. of para-dioxane and a solution of 15.82 g. (0.20 mole) of pyridine in 50 ml. of para-dioxane. There is obtained 52.9 g. (representing a yield of 84.5% of theoretical) of an oil which is identified by infrared, nuclear magnetic resonance, and mass spectroscopy analyses as 4,4'-bis(5-(nitrilecarbonato)-pentoxycarbonyloxy)-2,2-diphenylpropane, which can be represented by the structural formula:

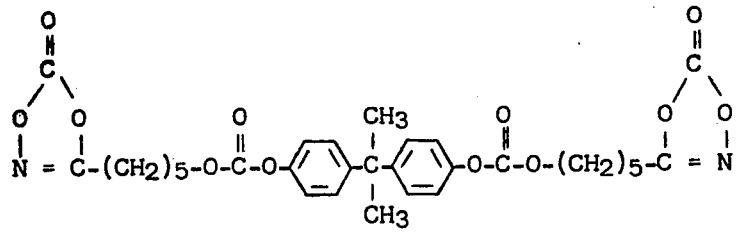

EXAMPLE V

A solution of 5.81 g. (0.04 mole) hexamethylene diamine and 5.30 g. (0.05 mole) sodium carbonate in 50 ml. water is added over a period of 45 minutes to a well-stirred solution of 25.25 g. (0.105 mole) of -(chlorocarbonyloxy) pentane-1-nitrile carbonate in 150 ml. of methanol-free chloroform at 25°C. The reaction mixture is stirred for another hour and the two layers are then separated after an additional amount of chloroform is added. The organic phase is washed with water, dried and evaporated to dryness under vacuum. The resulting white jelly is extracted twice with 250 ml. of diethyl ether at reflux for 0.52 hour. The product obtained is identified by infrared and nuclear magnetic resonance analyses as N,N'-bis(5-(nitrilecarbonato)-pentoxycarbonyl)-1,6-diaminohexane, which can be represented by the structural formula:

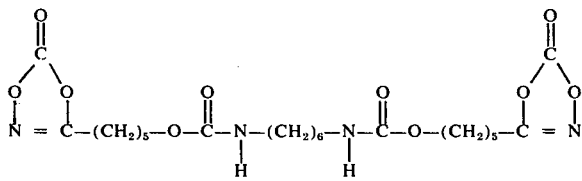

It is obtained of 18.7 g., representing 73 percent of the theoretical yield.

EXAMPLE VI

A solution of 3.00 g. (0.05 mole) ethylenediamine and 5.30 g. (0.05 mole) sodium carbonate in 30 ml. water is added over a period of 25 minutes to a well-stirred solution of 25.25 g. (0.105 mole) of 5-(chlorocarbonyloxy)pentane-1-nitrile carbonate in 150 ml. methanol-free chloroform at 25°C. The reaction mixture is stirred for another hour and the chloroform layer is separated, washed with water, dried and evaporated to dryness. The jelly residue is extracted with 250 ml. diethyl ether at reflux for 0.5 hour. The white solid product obtained is N,N'-bis(5-(nitrilecarbonato)pentoxycarbonyl)-1,2-diaminoethane, which can be represented by the structural formula:

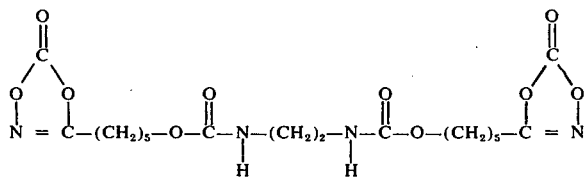

The product is obtained in an amount of 8.5 g., representing 37 percent of the theoretical yield.

EXAMPLE VII

In a manner similar to Example V, 4.30 g. (0.05 mole) of piperazine is reacted with 5-(chlorocarbonyloxy)pentane-1-nitrile carbonate to give 22.0 g. (representing 91 percent of the theoretical yield) of white, solid, N,N'-bis(5-(nitrilecarbonato)pentoxycarbonyl) piperazine, which can be represented by the structural formula:

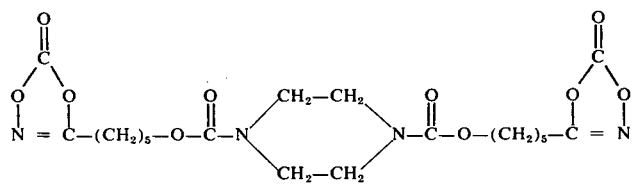

EXAMPLE VIII 2.35 grams (0.025 mole) of 1,2-ethanedithiol and 3.95 g. (0.05 mole) of pyridine are dissolved in 15 ml. of 1,4-dioxane and the solution is added in 25 minutes to a well-stirred solution of 11.78 g. (0.05 mole) of 5-(chlorocarbonyloxy)pentane-1-nitrile carbonate in 30 ml. of 1,4-dioxane. The temperature of the exothermic reaction is held with slight cooling at 26°–32°C. During the course of the reaction pyridine hydrochloride precipitates as a white solid. After the addition is complete, stirring of the reaction mixture is continued for 1 hour. The product mixture is dissolved in 150 ml. of chloroform and that solution is washed twice with ice water. The washed solution is dried over "Drierite" and the solvent evaporated under vacuum. 11.8 Grams (96% yield) of an oily product is obtained which is identified by infrared and nuclear magnetic resonance analyses as 1,2-bis(5-(nitrilecarbonato)pentoxycarbonylthio)ethane in 92.5 wt. % purity, which compound can be represented by the structural formula:

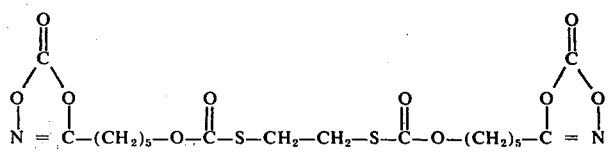

The main impurity is 5-chloropentane-1-nitrile carbonate.

EXAMPLE IX 3.056 Grams (0.025 mole) of 1,4-butanedithiol and 3.955 g. (0.05 mole) of pyridine are dissolved in 15 ml. of 1,4-dioxane and the solution is added in 20 minutes to a well-stirred solution of 11.78 g. (0.05 mole) of 5-(chlorocarbonyloxy)pentane-1-nitrile carbonate in 30 ml. of 1,4-dioxane. The temperature of the reaction mixture is held during the addition at 40°C. After the addition is complete, stirring of the reaction mixture is continued for 45 minutes at 46°C. and 50 minutes at 53°–55°C. The product mixture is dissolved in 150 ml. of chloroform and that solution is washed three times with ice water. The washed solution is dried over "Drierite" and the solvent is evaporated therefrom under vacuum. 11.7 Grams (90.8% yield) of an oily product is obtained which is identified by infrared and nuclear magnetic resonance analyses as 1,4-bis(5-nitrilecarbonato)pentoxycarbonylthio)butane in 80% purity, which compound can be represented by the structural formula:

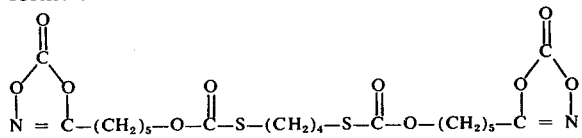

The main impurity is 5-chloropentane-1-nitrile carbonate.

EXAMPLE X 3.858 Grams (0.025 mole) of 1-mercapto-2-(mercaptoethylthio)ethane and 3.955g. (0.05 mole) of pyridine are dissolved in 15 ml. of 1,4-dioxane and the solution is added in 20 minutes to a well-stirred solution of 11.78g. (0.05 mole) of 5-(chlorocarbonyloxy)-pentane-1-nitrile carbonate in 30 ml. of 1,4-dioxane. The temperature of the reaction mixture during the addition is held at 40°C. After the addition is complete, stirring of the reaction mixture is continued for 1 hour at 55°–60°C. The product mixture is dissolved in 150 ml. of chloroform and that solution is washed three times with ice water. The washed solution is dried over "Drierite" and the solvent is evaporated therefrom under vacuum. 13.3 Grams (96.4% yield) of an oily product is obtained which is identified by infrared and nuclear magnetic resonance analyses as β,β'-bis(5-(nitrilecarbonato)pentoxycarbonylthio)ethylthioethane in 87.5 wt. % purity, which compound can be represented by the structural formula:

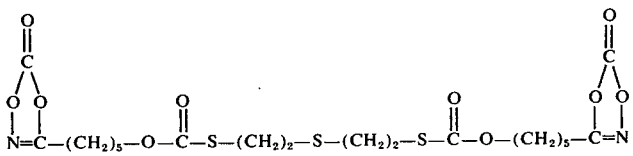

The main impurity is 5-chloropentane-1-nitrile carbonate.

EXAMPLE XI

The procedure of Example I is repeated except that 0.05 mole of 4-(chlorocarbonyloxy)-2-butene-1-nitrile carbonate is substituted for the 5-(chlorocarbonyloxy)-pentane-1-nitrile carbonate. A reaction product having the following structural formula is obtained:

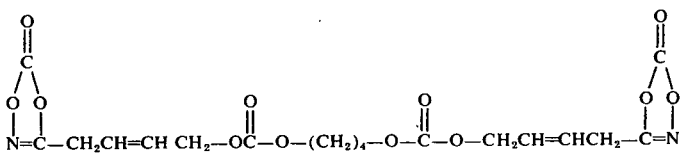

EXAMPLE XII

The procedure of Example I is repeated except that 0.05 mole of 6(chlorocarbonyloxy)3 hexyne-1-nitrile carbonate is substituted for the 5(chlorocarbonyloxy)-pentane-1-nitrile carbonate. A reaction product having the following sructural formula is obtained:

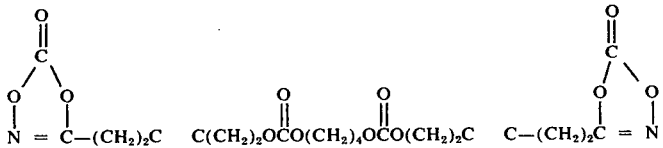

EXAMPLE XIII

The procedure of Example I is repeated except that 0.075 mole of 5-(chlorocarbonyloxy)-pentane-1-nitrile carbonate is reacted with 0.025 mole of polypropylene ether triol having a molecular weight of 3000 (sold by Union Carbide Co. under the trademark Niax Polyol LG56). A polymeric reaction product containing 3 nitrile carbonate groups per molecule of polypropylene ether is obtained.

EXAMPLE XIV

The procedure of Example I is repeated except that 0.0125 mole of N,N,N'N'-tetrakis(2-hydroxylpropyl)ethylene diamine (sold by Wyandotte Chemical Co., a subsidiary of BASF Co., under the trademark Quadrol) is substituted for the 1,4-butanediol. A product having the following structural formula is obtained:

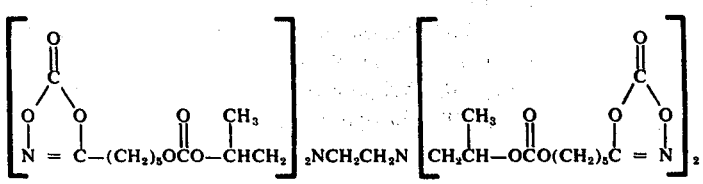

EXAMPLE XV

The procedure of Example I is repeated except that 0.022 mole of hydroxylated poly butadiene having an average of 2.3 hydroxyl groups per molecule and a molecular weight of 3000 is substituted for the 1,4-butane diol. A polymeric product containing about 2.3 nitrile carbonate groups per molecule of hydroxylated poly butadiene is obtained.

EXAMPLE XVI

The procedure of Example VI is repeated except that 0.05 mole of NN'bis(ethyl)ethylene diamine is substituted for the ethylenediamine. A product having the following structural formula is obtained:

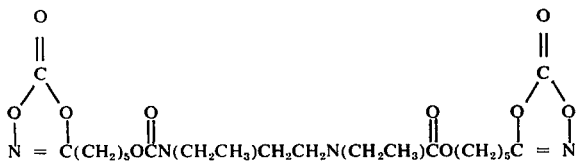

EXAMPLE XVII

The procedure of Example VII is repeated except that 0.05 mole of 3-amino piperidine is substituted for the piperazine. A reaction product having the following structural formula is obtained:

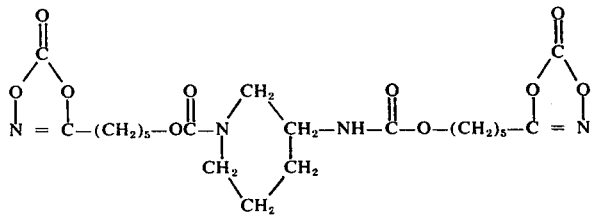

We claim:
1. A cyclic nitrile carbonate group-containing compound of the formula:

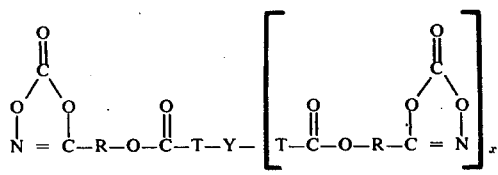

wherein R is aliphatic hydrocarbon of 2 to 11 carbon atoms, at least 2 carbon atoms of which separate the non-ring oxygen atom from the nitrile carbon atom, Y is an essentially hydrocarbonaceous organic radical free of groups that would be reactive with the nitrile carbonate groups and has a molecular weight of up to about 9,900, $x$ is 1 to 3 and T is O, S, NR' or

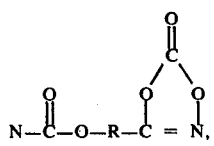

R' being hydrogen or an essentially hydrocarbonaceous organic radical free of groups that would be reactive with the cyclic nitrile carbonate groups having up to 10 carbon atoms, which radical is either monovalent and bonded only to the nitrogen atom of T, or is divalent and either (a) bonded to Y as well as to the nitrogen atom of T or (b) bonded to another nitrogen atom of another T as well as to said first nitrogen atom of said first T.

2. The compound of claim 1 wherein R has at least 3 carbon atoms and at least 3 carbon atoms thereof separate the non-ring oxygen atom from the nitrile carbon atom.

3. The compound of claim 2 wherein R is pentamethylene.

4. The compound of claim 2 wherein Y is tetramethylene and T is O or NH.

5. The compound of claim 2 wherein Y is hexamethylene and T is O or NH.

6. The compound of claim 2 wherein Y is dimethylene and T is S or NH.

7. The compound of claim 2 wherein Y is —CH$_2$—CH$_2$—S—CH$_2$—CH$_2$— and T is S.

8. The compound of claim 2 wherein Y is

and T is O.

9. The compound of claim 2 wherein Y is

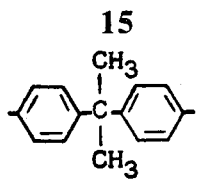
and T is O.
10. The compound of claim 1 wherein $x$ is 1 and T—Y—T is 3 amino piperidine.
11. The compound of claim 1 wherein $x$ is 1 and T—Y—T is piperazine.
* * * * *